US00PP17163P3

(12) United States Plant Patent
Redman

(10) Patent No.: US PP17,163 P3
(45) Date of Patent: Oct. 24, 2006

(54) ***CHRYSANTHEMUM* PLANT NAMED 'SWING TIME RED'**

(50) Latin Name: *Chrysanthemum morifolium*
Varietal Denomination: Swing Time Red

(75) Inventor: Ruth Redman, Bognor Regis (GB)

(73) Assignee: Cleangro, Ltd., Chichester (GB)

( * ) Notice: Subject to any disclaimer, the term of this patent is extended or adjusted under 35 U.S.C. 154(b) by 10 days.

(21) Appl. No.: 11/146,387

(22) Filed: Jun. 6, 2005

(65) Prior Publication Data

US 2005/0273898 P1 Dec. 8, 2005

Related U.S. Application Data

(60) Provisional application No. 60/578,007, filed on Jun. 7, 2004.

(51) Int. Cl.
*A01H 5/00* (2006.01)

(52) U.S. Cl. ..... Plt./286

(58) Field of Classification Search ..... Plt./286
See application file for complete search history.

(56) References Cited

U.S. PATENT DOCUMENTS

| | | | |
|---|---|---|---|
| PP14,896 P2 | 6/2004 | Boeder | Plt./298 |
| PP15,464 P2 | 1/2005 | Redman | Plt./286 |

*Primary Examiner*—Kent Bell
*Assistant Examiner*—Annette H Para
(74) *Attorney, Agent, or Firm*—Winston & Strawn, LLP

(57) ABSTRACT

A new variety of *Chrysanthemum* plant named 'Swing Time Red' having a good uniform canopy of red-bronze single type flowers and a light green disc. The new variety has medium vigor, free branching habit with good foliage presentation.

1 Drawing Sheet

Latin name of the genus and species: Botanical classification: *Chrysanthemum morifolium.*

Variety denomination: The new *Chrysanthemum* variety denomination is 'Swing Time Red'.

BACKGROUND OF THE INVENTION

The present invention comprises a new and distinct cultivar of *Chrysanthemum* botanically known as *Chrysanthemum morifolium,* and referred to by the variety name 'Swing Time Red'.

'Swing Time Red', identified as '20230-9', was discovered as a natural mutation of a whole plant in a controlled cultivated planting of the variety 'Swing Time Dark' (U.S. Plant Pat. No. 14,896). The variety 'Swing Time Red' has been asexually reproduced by vegetative cuttings at Chichester, West Sussex, United Kingdom, and the distinguishing characteristics are retained through successive generations of asexual reproduction.

BRIEF SUMMARY OF THE INVENTION

'Swing Time Red' is a pot type of *Chrysanthemum* plant variety having a slightly domed capitulum form and red bronze single flowers.

Comparison with Parent

Plant habit of the new *Chrysanthemum* variety 'Swing Time Red' is similar to the parent 'Swing Time Dark'. In side-by-side comparisons in Chichester, West Sussex, United Kingdom, under commercial practice, plants of the new *Chrysanthemum* variety 'Swing Time Red' differed from plants of the parent 'Swing Time Dark' in the following characteristics.

1. The new variety 'Swing Time Red' produces deep red bronze single flowers whereas the parent 'Swing Time Dark' produces dark orange single flowers.
2. Plants of the new variety 'Swing Time Red' have similar inflorescence to the plants of the parent 'Swing Time Dark'.

Comparison with Other Varieties

Plants of the new *Chrysanthemum* variety 'Swing Time Red' are similar to the variety 'Vulcan Time Bronze' (U.S. Plant Pat. No. 15,464) in plant habit and growth rate. In side-by-side comparisons in Chichester, West Sussex, United Kingdom, under commercial practice, plants of the new *Chrysanthemum* variety 'Swing Time Red' compared to plants of the variety 'Vulcan Time Bronze' in the following characteristics.

1. The flowers of the new variety 'Swing Time Red' are red bronze whereas the flowers of the variety 'Vulcan Time Bronze' are bronze.
2. The plants of the new variety 'Swing Time Red' have smaller and shorter inflorescence than the plants of the variety 'Vulcan Time Bronze'.

BRIEF DESCRIPTIONS OF ILLUSTRATIONS

FIG. 1 is a whole plant view of the new variety 'Swing Time Red' grown in a pot. The colors shown are as true as possible within the usual limits of this kind of illustration. The plant shown in the illustration is 60 days from the start of Short Days.

DETAILED BOTANICAL DESCRIPTION

The following description of the new *Chrysanthemum* variety 'Swing Time Red' is of plants grown in a greenhouse in Chichester, West Sussex, United Kingdom, in the month of June. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 18° C. at night and about 24° C. to 25° C. during the day under light conditions of about 5,000 to 6,000 foot candles. The plants respond well to the use of growth retardant, such as three B9 treatments at 2 gm per liter. To produce a commercial product the plants may be pinched once. The typical container size for commercial growth is 1 liter. It has been observed that the shelf life of the new variety is about 21 days with a response time of about 7.5 weeks. The new variety is suitable for growth in a temperature range of 15° C. to 25° C.

The following description is with respect to a plant produced as a pot *Chrysanthemum.* In the description of this new *Chrysanthemum* variety, color values have been taken from The Royal Horticultural Society Colour Chart (R.H.S.C.C).

Plant

Plant type: Pot.
Habit: Upright and branching.
Height: 24 cm.
Width: 32 cm.
Stem:
- *Length* (*cm*).—6.
- *Diameter* (*cm*).—0.5.
- *Texture.*—Slightly pubescent.
- *Color.*—137B.

Branching characteristics: Upright and free branching.
Lateral branches:
- *Length* (*cm*).—12.
- *Diameter* (*cm*).—0.5.
- *Texture* (*cm*).—Slightly pubescent.

Number of breaks from pinch: 5.
Stem color: 137B.
Response time: 54 days.
Vigor: Medium.
Shelf life: 21 days.
Life of blooms: 21 days.
Disease (susceptibility or resistance observed): None observed.
Pest (resistance or susceptibility): None observed.
Drought and temperature (susceptibility or resistance observed): None observed.
Growth retardant type and treatment: 3 applications of 2.5 grams/liter at 2 days, 21 days and 28 days after sticking of unrooted cuttings.

The plants were grown for two weeks in Long Day conditions (20 hours of light) and then transferred to Short Day conditions (13 hours of dark).

Propagation:
- *Type.*—Vegetative propagation via stem cuttings.
- *Time to rooting.*—12–14 days with soil temperatures of 18° C.
- *Rooting habit.*—Fine and fibrous.

Foliage

Number of leaves per lateral branch: 12.
Compound or single: Single.
Arrangement of leaves: Alternate.
- *Shape of leaf.*—Typically 5 lobed.
- *Size of leaf.*—Width (cm): 6; Length (cm): 8.
- *Leaf apex.*—Rounded.
- *Base.*—Cordate.
- *Attachment.*—Petioled.
- *Aspect.*—Slightly undulating.
- *Margin.*—Palmately lobed.
- *Surface characteristics.*—Top: slightly pubescent. Bottom: pubescent.

Petiole:
- *Color.*—137C.
- *Length* (*cm*).—0.8.
- *Diameter* (*cm*).—0.2.

Venation:
- *Color.*—Upper side: 137B. Under side: 137D.

Color:
- *Mature leaf, upper side.*—137A; under side: 137D.
- *Young leaf, upper side.*—138A; under side: 137C.

Flower

Flower appearance: Matte.
Flower type: Single.
Flower form: Slightly cupped.
Flower shape: Circular.
Flowering habit: Cyme.
Number of blossoms per branch: 5.
Inflorescence form: Cyme.
- *Depth of fully expanded blossoms* (*cm*).—1.5.
- *Diameter of fully expanded blossoms* (*cm*).—6.

Phyllaries:
- *Number.*—20–25.
- *Color.*—137B.
- *Length* (*cm*).—0.8.
- *Width* (*cm*).—0.2.
- *Texture/appearance.*—Pubescent.

Peduncle:
- *Length* (*cm*).—10.
- *Diameter* (*cm*).—0.5.
- *Angle from stem* (*degrees*).—25.
- *Color.*—137B.
- *Surface.*—Slightly pubescent.
- *Habit.*—Slightly undulating.
- *Strength.*—Moderately strong.

Pedicel:
- *Length.*—Terminal (*cm*): 4; Lateral (cm): 6.
- *Diameter* (*cm*).—0.2.
- *Color.*—Near 137B.
- *Surface.*—Pubescent.
- *Habit.*—Slightly undulating.
- *Strength.*—Moderately strong.

Ray florets:
- *Form/shape.*—Straight with parallel edges.
- *Texture/appearance.*—Matte.
- *Number per flower.*—35.
- *Length* (*cm*).—4; Width (cm): 0.8.
- *Apex.*—Rounded.
- *Base.*—Tapered.
- *Margin.*—Entire.

Disc florets:
- *Form/shape.*—Cylindric.
- *Texture/appearance.*—Shiny.

*Number per flower.*—>150.
*Length* (*cm*).—0.4; Width (cm): 0.1.
*Diameter of disc* (*cm*).—1.6.

Fragrance: None observed.

Flower bud (at onset of color):
*Length* (*cm*).—0.8.
*Diameter* (*cm*).—1.
*Form/shape.*—Globular.

General flower color:
1. *Ray florets, upper side.*—Immature: 43A. Mature: 43B. Older/Fading: 40C. Ray florets, under side: Immature: 26A. Mature: 26B. Older/fading: 26C.
2. *Disc florets.*—Immature: 151A. Mature: 7A. Older/fading: 7A.
4. *Bud.*—26A.

Flower progression with age: Flower form does not change but the flower color fades slightly with age.

Reproductive Organs

Gynoecium: Present on both Ray and Disc florets.

Ray florets per individual flower: Pistillate:
*Pistil number.*—35.
*Stigma color.*—Near 6C.
*Stigma shape.*—Forked.
*Style length* (*cm*).—0.5.

Disc florets per individual flower: Pistillate:
*Pistil number.*—160 to 200.
*Stigma color.*—Near 6C.
*Stigma shape.*—Forked.
*Style length* (*cm*).—0.1.

Androecium: Present on disc florets only: Staminate:
*Stamen number.*—>50.
*Anther shape.*—Clubbed.
*Anther color.*—15B.
*Pollen quantity.*—Medium.
*Pollen color.*—15A.

Fruit and seeds: None observed.

What is claimed is:

1. A new and distinct variety of *Chrysanthemum* plant, substantially as described and illustrated herein.

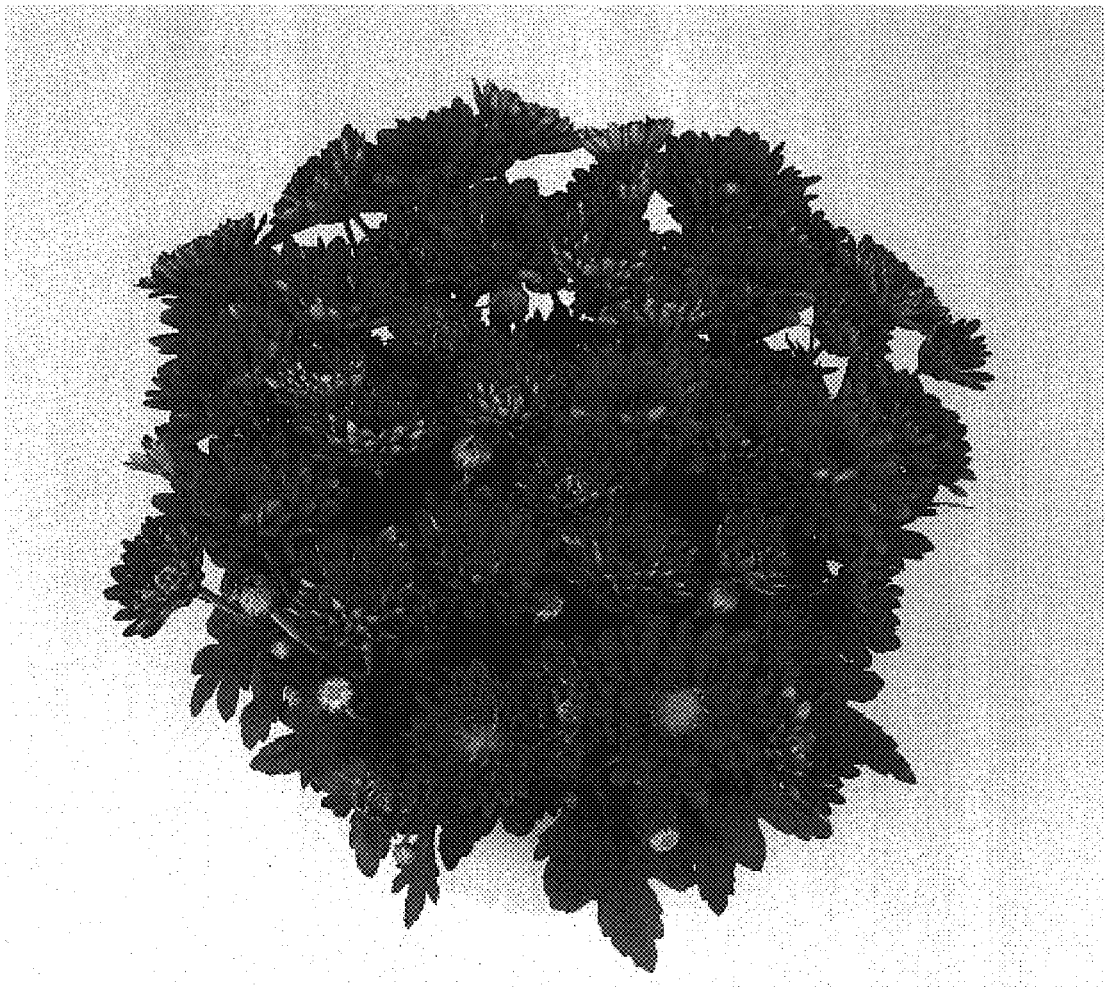

* * * * *